(12) United States Patent
Shaver et al.

(10) Patent No.: US 7,914,532 B2
(45) Date of Patent: Mar. 29, 2011

(54) ORTHOPEDIC ROD WITH LOCKING APERTURE

(75) Inventors: Joseph A. Shaver, St. Helens, OR (US);
Bryon M. Morse, Milwaukie, OR (US);
Steven P. Horst, Dayton, OR (US);
Randall J. Huebner, Beaverton, OR (US)

(73) Assignee: Acumed LLC, Hillsboro, OR (US)

( * ) Notice: Subject to any disclaimer, the term of this patent is extended or adjusted under 35 U.S.C. 154(b) by 1170 days.

(21) Appl. No.: 11/585,378

(22) Filed: Oct. 23, 2006

(65) Prior Publication Data

US 2007/0123878 A1 May 31, 2007

Related U.S. Application Data

(60) Provisional application No. 60/729,373, filed on Oct. 21, 2005.

(51) Int. Cl.
*A61B 17/56* (2006.01)

(52) U.S. Cl. ............................................ 606/62; 606/64

(58) Field of Classification Search .................... 606/62, 606/64, 291
See application file for complete search history.

(56) References Cited

U.S. PATENT DOCUMENTS

| | | | |
|---|---|---|---|
| 4,135,507 A | 1/1979 | Harris | |
| 4,475,545 A | 10/1984 | Ender | |
| 4,503,847 A | 3/1985 | Mouradiam | |
| 4,522,202 A | 6/1985 | Otte et al. | |
| 4,622,959 A | 11/1986 | Marcus | |
| 4,697,585 A | 10/1987 | Williams | |
| 5,034,013 A | 7/1991 | Kyle | |
| 5,035,697 A | 7/1991 | Frigg | |
| 5,066,296 A | 11/1991 | Chapman et al. | |
| 5,248,313 A | 9/1993 | Greene et al. | |
| 5,441,500 A | 8/1995 | Seidel | |
| 5,472,444 A | 12/1995 | Huebner et al. | |
| 5,480,402 A | 1/1996 | Kim | |
| 5,713,901 A | 2/1998 | Tock | |
| 5,776,194 A | 7/1998 | Mikol et al. | |
| 5,779,705 A | 7/1998 | Matthews | |
| 5,814,047 A | 9/1998 | Emilio et al. | |
| 5,954,722 A | 9/1999 | Bono | |

(Continued)

FOREIGN PATENT DOCUMENTS

EP 355411 2/1990

OTHER PUBLICATIONS

Bray, Timothy J., ed., "Techniques on Fracture Fixation as Practiced by the Reno Orthopaedic Clinic," Gower Medical Publishing, New York 1993.

(Continued)

*Primary Examiner* — Eduardo C Robert
*Assistant Examiner* — Elana B Fisher
(74) *Attorney, Agent, or Firm* — Kolisch Hartwell, PC

(57) ABSTRACT

System, including methods and apparatus, for treating orthopedic conditions using a rod member structured for placement in a medullary canal of a bone and including at least one locking aperture with an internal thread structure. In some embodiments, the internal thread structure may include two or more thread leads disposed adjacent the same end of the locking aperture, two or more interspersed internal threads, and/or a thread depth substantially less than that of a corresponding threaded fastener for the locking aperture.

14 Claims, 3 Drawing Sheets

U.S. PATENT DOCUMENTS

| | | | |
|---|---|---|---|
| 6,019,761 | A | 2/2000 | Gustilo |
| 6,123,708 | A | 9/2000 | Kipela et al. |
| 6,355,043 | B1 * | 3/2002 | Adam ........................... 606/62 |
| 6,402,753 | B1 | 6/2002 | Cole et al. |
| 6,508,820 | B2 | 1/2003 | Bales |
| 6,517,541 | B1 | 2/2003 | Sesic |
| 6,579,294 | B2 | 6/2003 | Robioneck |
| 6,652,529 | B2 | 11/2003 | Swanson |
| 6,692,496 | B1 | 2/2004 | Wardlaw |
| 6,793,659 | B2 | 9/2004 | Putnam |
| 7,135,044 | B2 * | 11/2006 | Bassik et al. ............... 623/22.42 |
| 7,655,009 | B2 * | 2/2010 | Grusin ........................... 606/64 |
| 2004/0193155 | A1 * | 9/2004 | Castaneda ...................... 606/60 |
| 2005/0234472 | A1 | 10/2005 | Huebner |
| 2006/0095039 | A1 * | 5/2006 | Mutchler ....................... 606/64 |

OTHER PUBLICATIONS

Declaration of Michael W. Chapman, M.D.; Reexamination of U.S. Patent No. 5,472,444 to Huebner et al.
DePuy, "The Chandler Tibial Nail" product information sheets, 1990.
File History of U.S. Patent No. 5,472,444 Reexamination Proceeding, U.S. Appl. No. 90/007,923, filed Feb. 10, 2006.
Ingman, A.M., "A New Locked Nail for Proximal Humeral Fractures," J. Bone Joint Surg. (1994) 76-B, Supp. II and III, Australian Orthopaedic Association, Sep. 24-28, 1993, p. 119.
Kozin, Scott Hal, M.D. and Anthony Clayton Berlet, M.D., "Handbook of Common Orthopaedic Fractures," 4th ed., Medical Surveillance Inc., Willow Grove 2000.
Plaintiff's First Supplemental Response to Defendant's First Set of Interrogatories (Nos. 1, 4, 6, 10 and 13); *Acumed LLC* v. *Smith & Nephew, Inc.*, U.S. District Court for the District of Oregon, Case No. CV 04-1498BR, Mar. 2, 2005.
Thompson, Jon C., M.D., Netter's Concise Atlas of Orthopaedic Anatomy, Icon Learning Systems LLC, Teterboro 2002.
Miller, ME et al., Three surgical approaches to the different portions of the humeras, Manual of Internal Fixation Techniques, 1979.
Alta, Modular Trauma System, The Howmedica Alta IM Rod Surgical Technique, 1990.
Intermedics Orthopedics, Inc., The Intermedics Select Shoulder System Product Guide, 1990.
Jakob et al., The Journal of Bone and Joint Surgery, Four Part Valgus Impacted Fractures of the Proximal Humeras, vol. 73-B, No. 2, Mar. 1991.
Orthopedics Today, Clinical numbers needed to decide which really is best, vol. 13, No. 9. p. 1, 20, 21, Sep. 1993.
Styker, Annual Report, 2003.
Stryker Trauma, Stryker T2 IM Nailing System Product Guide, 2003.
T2 Proximal Humeral Nailing System Surgical Protocol Brochure, 2004.
Ace, AIM Titanium Femoral Nail System Surgical Technique Informational Guide, no date provided.
Ace, AIM Titanium Tibial Nail Informational Guide, no date provided.
Acumed, Polarus Humeral Rod System Informational Guide, no date provided.
Applied Osteo Systems, Inc., True/Flex Torsionally Resistant Upper Extremity/Flexible Product Catalog, no date provided.
Biomet, Inc., Stainless Steel Taper, Small Bone Locking Nail Product Guide, no date provided.
Biomet, Inc., The Uniflex Nailing System, The Complete System for Intramedullary Femoral Fixation, no date provided.
Biomet, Inc., Uniflex Humeral Nail System Product Guide, no date provided.
Howmedica Surgical Techniques, Alta Tibial/Humeral Rod Surgical Technique, no date provided.
Howmedica, Alta Modular Trauma System Tibial/Humeral IM Rod Tibial Applications Product Guide, no date provided.
Howmedica, Gamma Locking Nail System Product Guide and Catalog, no date provided.
Intermedics Orthopedics, Inc., The Intermedics Select Shoulder System Product Guide, no date provided.
Smith and Nephew, Trigen Humeral Nail System, no date provided.
Stryker Trauma, T2 Proximal Humeras Engineering Perspective, no date provided.

* cited by examiner

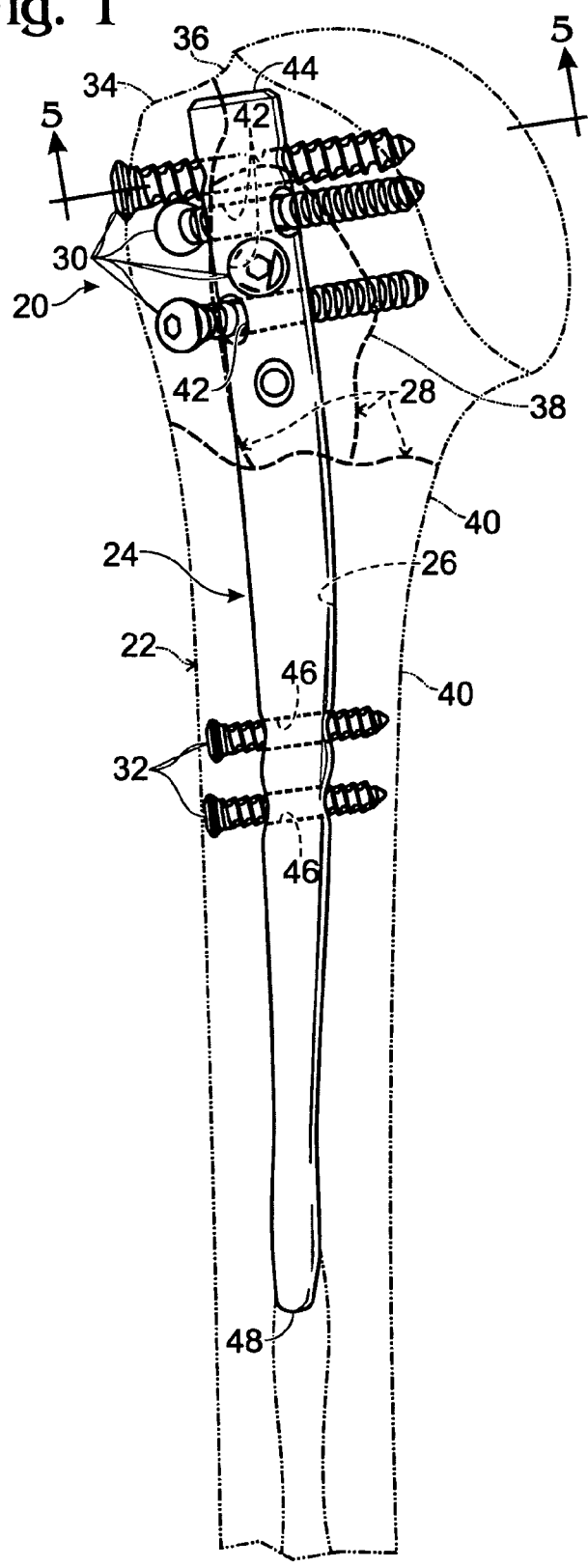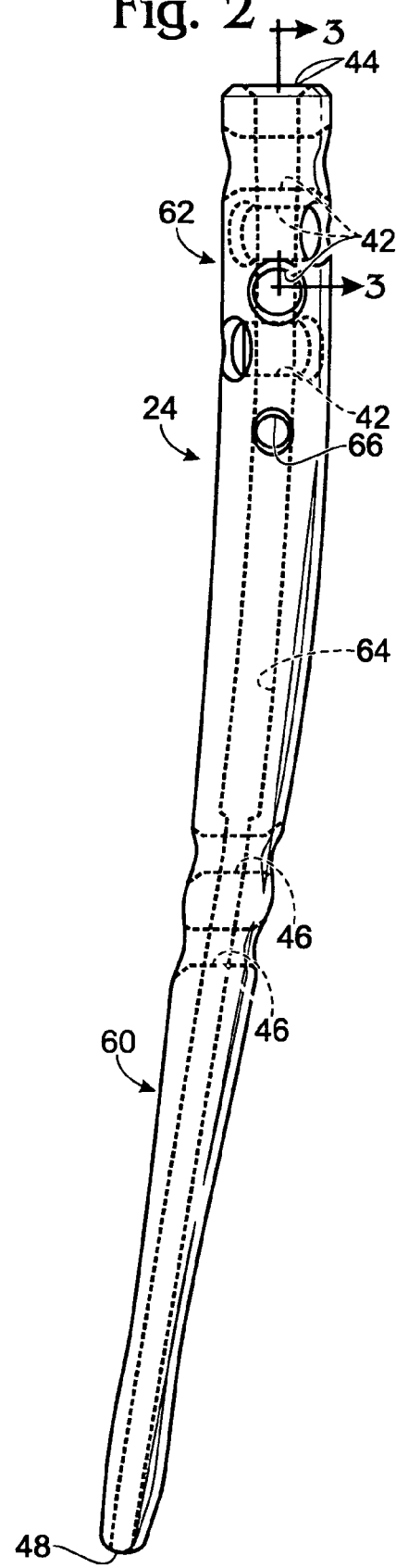

ORTHOPEDIC ROD WITH LOCKING APERTURE

CROSS-REFERENCE TO PRIORITY APPLICATION

This application is based upon and claims the benefit under 35 U.S.C. §119(e) of U.S. Provisional Patent Application Ser. No. 60/729,373, filed Oct. 21, 2005, which is incorporated herein by reference in its entirety for all purposes.

INTRODUCTION

The human skeleton is composed of 206 individual bones that perform a variety of important functions, including support, movement, protection, storage of minerals, and formation of blood cells. To ensure that the skeleton retains its ability to perform these functions, and to reduce pain and disfigurement, bones that become fractured should be repaired promptly and properly. Typically, a fractured bone is treated using a fixation device, which reinforces the fractured bone and keeps it aligned during healing. Fixation devices may take a variety of forms, including casts and fixators for external fixation, and rods, bone plates, and/or fasteners (screws, pins, wires, etc.), for internal fixation, among others.

Orthopedic rods may function as fixation devices (e.g., intramedullary rods/nails) and/or in prosthetic devices (e.g., stem portions thereof), among others, received in the medullary canal of a broken and/or cut bone. For installation of the orthopedic rod, the medullary canal may be accessed from an end and/or side of the bone with an instrument such as an awl, drill, or saw. The medullary canal also may be prepared to receive the orthopedic rod, for example, by reaming and/or broaching, to enlarge and/or shape the canal. After rod placement into the canal, the rod may be secured in position using fasteners, for example, by attaching the rod to only one fragment or, in the case of fixation, to two or more bone fragments disposed on opposing sides of a break or cut in the bone. The rod thus may include a plurality of apertures (holes) that receive threaded fasteners, such as bone screws, which may be anchored in bone adjacent each aperture via an external thread.

Each aperture within a rod may be nonlocking (e.g., without a thread) or locking (e.g., with a thread). A locking aperture may engage a suitable corresponding fastener such that translational movement of the fastener in both opposing directions along the aperture is restricted; in contrast, a nonlocking aperture generally permits this translational movement. Of these two types, nonlocking apertures may be relatively easy for a surgeon to use because a nonlocking aperture generally can receive a threaded fastener that is aligned with the aperture, irrespective of the relative rotational disposition of the fastener and the aperture. However, nonlocking apertures may be less effective for fixing the rod, threaded fasteners, and/or bone in position.

Locking apertures of a rod may be more difficult for a surgeon to use. In particular, because a locking aperture is spaced from the bone surface by bone, a threaded fastener that is advanced rotationally into the bone from the bone surface may arrive at the locking aperture at an unsuitable rotational (and thus axial) disposition relative to an internal thread of the aperture. The threaded fastener thus may not thread readily into the aperture. Accordingly, the threaded fastener may be hard to turn and/or may create an undesirable sound (such as squeaking), among others, during fastener advancement after the fastener is forced into registration with the locking aperture. Furthermore, bone may be damaged (e.g., a thread formed in bone may be stripped) as the threaded fastener is forced into registration. This problem may be compounded by the use of bone screws having a deep external thread (and thus a relatively large pitch) for engagement with cancellous bone.

SUMMARY

The present teachings provide a system, including methods and apparatus, for treating orthopedic conditions using a rod member structured for placement in a medullary canal of a bone and including at least one locking aperture with an internal thread structure. In some embodiments, the internal thread structure may include two or more thread leads disposed adjacent the same end of the locking aperture, two or more interspersed internal threads, and/or a thread depth substantially less than that of a corresponding threaded fastener for the locking aperture.

BRIEF DESCRIPTION OF THE DRAWINGS

FIG. 1 is an anterior view of an exemplary orthopedic implant system installed in a humerus bone and including an intramedullary rod disposed in and extending along the medullary canal of the humerus bone, with the rod including a plurality of proximal apertures each having a multi-threaded structure, in accordance with aspects of the present teachings.

FIG. 2 is a side elevation view of the intramedullary rod of FIG. 1 taken in the absence of bone and fasteners, in accordance with aspects of the present teachings.

DETAILED DESCRIPTION

Figure 3:
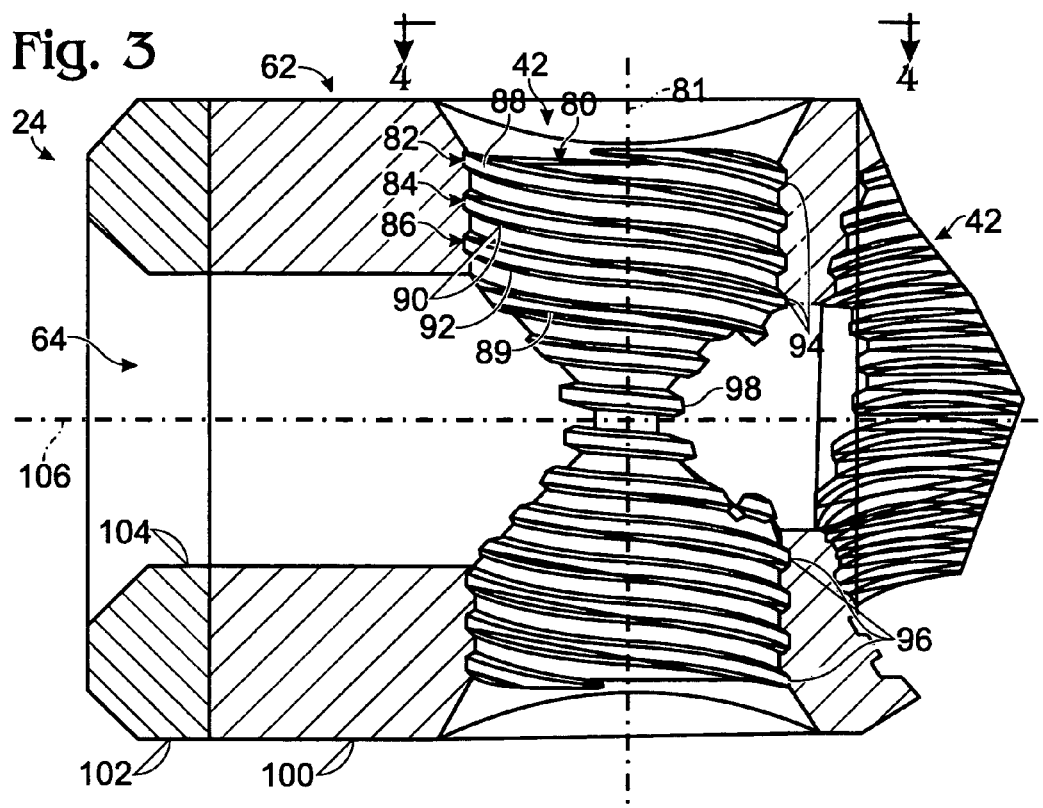
FIG. 3 is a fragmentary sectional view of the intramedullary rod of FIG. 2, taken generally along line 3-3 of FIG. 2.

The present teachings provide a system, including methods and apparatus, for treating orthopedic conditions using a rod member structured for placement in a medullary canal of a bone and including at least one locking aperture with an internal thread structure. In some embodiments, the internal thread structure may include two or more thread leads disposed adjacent the same end of the locking aperture, two or more interspersed internal threads, and/or a thread depth substantially less than that of a corresponding threaded fastener for the locking aperture.

FIG. 1 shows an anterior view of an exemplary orthopedic implant system 20 installed in a fractured humeral bone 22. (The humerus is shown here in phantom outline to emphasize the implant system; in other embodiments, the implant system may be installed in other bones.) System 20 may include an orthopedic rod 24, such as an intramedullary rod, shown here, for bone fixation, or a supporting stem of an orthopedic prosthesis for replacement of a section of bone, among others. The orthopedic rod may be disposed in medullary canal 26 of the humeral bone with the rod extending along the medullary canal. Rod 24 may be disposed completely in the medullary canal (i.e., completely interior to the bone) or disposed only partially in the medullary canal with a portion (e.g., a minor fraction) of the rod projecting from the bone after installation. The medullary canal may be unmodified, may be modified by injury (e.g., trauma), and/or may be prepared for receiving the rod by reaming, broaching, etc. Furthermore, rod 24 may span one or more discontinuities, such as one or more fractures 28 in a humeral bone.

System 20 also may include a plurality of threaded (and/or nonthreaded) fasteners, such as bone screws 30, 32 for connecting rod 24 to bone via transverse apertures of the rod. The fasteners may be disposed in only one bone fragment (such as when the rod is part of a prosthesis installed in a truncated bone to replace the head of the bone) or may connect a plurality of fragments, such as humeral fragments 34-40, to the rod. Furthermore, the fasteners (and/or apertures) may be of the same or different sizes (compare bone screws 30 and 32 having different lengths, diameters, and thread pitches).

The transverse apertures for receiving fasteners may include or lack internal thread structure. In other words, each transverse aperture may be a locking aperture or a nonlocking aperture. For example, the transverse apertures may include one or more proximal or trailing apertures 42 disposed closer to a proximal/trailing end 44 of the rod and each having (or lacking) one or more internal threads for threaded engagement with bone screws 30, such that the apertures are locking (or nonlocking). Alternatively, or in addition, the transverse apertures may include one or more distal or leading apertures 46 disposed centrally and/or closer to a distal/leading end or tip 48 of the rod. Apertures 46 may lack (or have) internal thread structure, such that the apertures are nonlocking (or locking).

The internal thread structure of a locking aperture may facilitate threaded engagement with a fastener that is threaded into the rod aperture. For example, the locking aperture(s) of a rod may be multi-threaded, with two or more internal threads defining two or more alternative start sites (thread leads) and threading paths for an external thread of a fastener advanced into the aperture. The internal threads thus may have the same pitch. In addition, the internal threads may be adjacent and/or interspersed with one another along the aperture by being offset relative to one another along the locking aperture by a distance less than the pitch of the threads. Accordingly, axial misregistration of the external and internal threads may be reduced relative to a single-threaded aperture (e.g., see Example 2 of Section VII). Alternatively, or in addition, the locking aperture may have a relatively shallow internal thread(s) that mates with a substantially deeper external thread(s) of a fastener.

Overall, the present teachings may provide orthopedic rods that threadably receive fasteners with (1) improved threadability, (2) less damage to bone, (3) increased or more stable threaded engagement between the fasteners and bone, (4) less effort required for installation and/or removal (for example, less torque needed to turn the fasteners), (5) a reduced tendency for the fasteners to jam, stick, or squeak during installation, and/or (6) less wear on thread surfaces.

These and other aspects of the present teachings are described below, including, among others, (I) orthopedic rods, (II) locking apertures, (III) fasteners, (IV) composition of system components, (V) installation of orthopedic rods, (VI) kits, and (VII) examples.

I. Orthopedic Rods

An orthopedic rod, as used herein, is any rod-like member configured to be disposed at least substantially, at least mostly, or completely in a medullary canal of a bone, generally such that the rod extends along the medullary canal (i.e., extending substantially parallel to a regional long axis of the canal). The orthopedic rod may be used to treat any suitable orthopedic condition, for example, to fix and/or stabilize a broken and/or cut bone, to fix adjacent bones for fusion, to support a prosthetic element (such as a prosthetic head for a bone), and/or the like.

The orthopedic rod may have any suitable dimensions, including any suitable length and cross-sectional dimension(s) (e.g., width, diameter, and/or thickness). The length of the rod may be selected, for example, according to the size and condition of the bone(s) to be treated, such that the rod may extend along any suitable portion of a medullary canal and/or bone. In some examples, the rod may extend less than or greater than about one-fourth, one-half, and/or three-fourths of the length of the canal and/or bone, or may have a length that is about the same as or is greater than the length of the canal and/or bone. The diameter of the rod may be selected, for example, according to the cross-sectional size of a medullary canal into which the rod is to be inserted, either with or without peri-operative widening of the canal by removal of a portion of adjacent bone (such as by reaming, broaching, sawing, etc.). For example, a rod of greater diameter may be selected for a wider canal, and a rod of lesser diameter selected for a narrower canal. The diameter of the rod may be about the same as the diameter of the canal, so that the rod fits at least relatively closely into the canal. More particularly, the canal may be at least slightly wider than the rod (e.g., for ease of rod placement and/or to allow rod wobble and/or lateral positioning), or may be at least slightly narrower than the rod (e.g., to provide a tight fit and thus restrict rod and/or bone fragment migration). The diameter of the rod may be uniform or may vary along the rod. For example, the rod may be narrower toward one or both of its ends (such as through one or more stepwise decreases in diameter and/or through a tapered decrease(s)).

The orthopedic rod may have any suitable shape. The rod may be elongate, for example, having a length that is at least about five or ten times the diameter of the rod. The rod may have any suitable cross-sectional shape, including circular, noncircular (e.g., oval, polygonal, etc.), rosette, and/or the like. In some examples, the cross-sectional shape may be determined, at least in part, by one or more projections or depressions (e.g., ridges and/or grooves) formed on the side of the rod. The cross-sectional shape may be substantially uniform or may vary along the length of the rod. The rod may be linear or may be nonlinear (bent) to define a curved and/or angular path. In some examples, the rod may have at least one linear section and at least one nonlinear section disposed along its long axis. The rod also may be somewhat flexible to permit changes to its longitudinal shape according to the range of longitudinal shapes of canals into which the rod may be placed.

The orthopedic rod may have a smoothly contoured surface and/or may have any suitable surface features. In some examples, the rod may have one or more projections (e.g., bumps, tines, ridges, etc.) and/or depressions (e.g., dimples, flutes, etc.) disposed on the exterior surface of the rod. The projections and/or depressions may be formed on a leading section, a central section, a trailing section, and/or one or both opposing ends of the rod, and/or may be disposed substantially along the entire length of the rod. The depressions and/or projections may extend along and/or around the rod, for example, to form annular, helical, and/or longitudinal ridges or flutes. The exterior (and/or interior) surface of the rod may have any suitable coefficient of friction, for example, the exterior surface may be textured or roughened to restrict slippage in bone or may be smooth to facilitate placement into bone.

The orthopedic rod may have any suitable structure, number, and type of apertures (openings), at any suitable position (s). The apertures may extend linearly or nonlinearly, and may extend longitudinally and/or transversely relative to the rod. A transverse aperture may be configured to be disposed adjacent diaphyseal (e.g., shaft) or metaphyseal (e.g., head) bone. Transverse apertures may define axes disposed at different positions and/or at the same position along the long axis of the rod. The axes may be parallel or nonparallel. Nonparallel axes may be offset from one another by rotation about a long axis and/or a transverse axis of the rod. Each transverse aperture may be locking or nonlocking, that is, configured, respectively, to restrict or to permit translational movement of a corresponding fastener along the aperture. Furthermore, each transverse aperture may be non-elongate (e.g., circular) or elongate (e.g., oval).

The orthopedic rod may have any suitable number of components. The orthopedic rod may be unitary (one piece) or may be formed of two or more rod components. The two or more rod components may have any suitable arrangement. For example, the rod components may be arranged end to end (such as rod components that are attached fixedly or movably to one another (e.g., that thread to one another to increase the overall length of the rod)). Alternatively, or in addition, one or more of the rod components may be disposed at least partially inside or outside another rod component. For example, one or more of the rod components may be a sheath (or core) disposed on the exterior (or in the interior) of another rod component.

Further aspects of orthopedic rods that may be suitable for the implant systems of the present teachings are described in U.S. Pat. No. 5,472,444, issued Dec. 5, 1995, and U.S. Pat. No. 6,494,913, issued Dec. 17, 2002, each of which is incorporated herein by reference.

II. Locking Apertures

An orthopedic rod may include one or more locking apertures. The locking apertures may have any suitable structure and any suitable position(s) in the rod.

The locking apertures may have any suitable size and shape. The locking apertures of a rod may have the same length and/or width, or may be of different lengths and/or widths. The lengths may differ, for example, if the apertures are disposed at positions along a rod having a nonuniform cross-sectional size and/or if the apertures define angles of different magnitude with the long axis of the rod. The diameters of the apertures may differ, for example, if the apertures are configured to be engaged with fasteners of different diameter. Locking apertures may have any suitable cross-sectional dimension, with exemplary diameters of about 1-10 millimeters. In exemplary embodiments, intended only for illustration, the locking apertures may have diameters that accommodate and/or provide threaded engagement with bone screws of any the following diameters: 1 mm, 1.5 mm, 2.0 mm, 2.7 mm, 3.5 mm, 4.0 mm. 5.3 mm, 6.5 mm, or 8 mm, among others. The locking apertures may have any suitable cross-sectional shape. For example, the locking apertures may be substantially circular or may be noncircular. Exemplary locking apertures with a noncircular cross section may be configured to engage a fastener at only one lateral position or at two or more lateral positions across each aperture.

The locking apertures may be disposed at any suitable position(s) in the rod. In some examples, the locking aperture (s) may be disposed toward one of the ends of the rod. For example, the locking aperture(s) may be configured to be disposed adjacent metaphyseal bone, that is, in or near the head of a bone. The locking apertures may define axes disposed at different positions (or at substantially the same position) along the length of the rod. Alternatively, or in addition, the locking apertures may define axes that are parallel or nonparallel. Nonparallel axes may be offset from one another by rotation about a long axis and/or a transverse axis of the rod.

A locking aperture may have any suitable locking structure that engages the fastener by rotational motion of the fastener and/or the aperture, to restrict axial movement of the fastener along the aperture, generally in both opposing directions parallel to the long axis of the fastener. In exemplary embodiments, the locking structure may be defined by one or more internal threads (helical or oblique (helix-like) depressions (e.g., helical flutes/grooves)), and/or the fastener may include one or more external threads (helical or oblique (helix-like) projections (e.g., helical ribs/ridges)). Each thread may be continuous or may be interrupted, such that the thread includes a plurality of discrete thread segments each extending along discrete portions of the same helical path. In some examples, only the aperture (or the fastener) includes a thread, and the fastener (or the aperture) includes a nonhelical projection(s) (or depression(s)) that provides threaded engagement with the thread of the aperture (or fastener).

A locking aperture may include a plurality of internal threads. The threads may be disposed in an interspersed relationship in the aperture, to form a multi-threaded aperture. Threads are interspersed (or overlap), as used herein, when there is overlap in the axial (longitudinal) ranges of the threads (as measured between opposing ends of each thread parallel to the central axis of the aperture). In contrast, the threads are not interspersed when their longitudinal ranges do not overlap. Interspersed threads may be intersecting (such that the threads cross one another) or may be non-intersecting. Interspersed threads (and/or an external thread of a fastener) may have any suitable pitch, such as a pitch of about 0.2 mm to 4 mm. Interspersed threads (and/or an external thread of a fastener) may have any suitable thread depth (generally, defined as one-half of the difference between the major and minor diameters of an aperture or fastener shank), such as a thread depth of about 0.1 mm to 4 mm. Interspersed threads may have the same or different pitches, thread depths, thread widths (measured parallel to the central axis of the aperture), and/or thread lengths. Furthermore, within each thread of an interspersed set, the thread depth, width, cross-sectional shape, land width, and/or pitch may be uniform or nonuniform. For example, the thread may have a thread width, depth, and/or land width that tapers away from and/or toward an entry side of the aperture.

Further aspects of locking apertures are described elsewhere in the present teachings, such as in Section VII, among others.

III. Fasteners

The orthopedic rods of the present teachings may be used with any suitable fasteners. Exemplary fasteners include screws, wires, pins, clips, clamps, etc. Locking apertures may be used with fasteners that extend into, engage, and lock to the apertures.

Exemplary threaded fasteners for use with locking apertures may be bone screws. A bone screw generally includes a head and a shank. The head may provide a recessed and/or projecting engagement structure for rotation by a driver and/or may include an enlarged portion that restricts advancement of the bone screw (e.g., by engagement with a bone surface). The shank may include an external thread that extends over any suitable portion (e.g., a leading portion, a central portion, and/or a trailing portion) or substantially all of the length of the shank.

The threaded fastener may have any suitable size, including length, diameter, pitch, thread depth, and/or thread shape, among others. Generally, the threaded fastener may be selected to correspond to a locking aperture of a rod and to bone in which the rod is placed. The length may be selected to extend approximately from an exterior surface region of a bone, at least partially or completely into and/or through a corresponding rod (and locking aperture), and, optionally, beyond the rod into and/or through bone. Accordingly, the threaded fastener may have a length that is greater than at least about half the diameter of the bone (where the threaded fastener is to be installed) and/or that is about the same as the bone diameter. The threaded fastener may have any suitable diameter. The diameter may be selected to correspond to the diameter (or other characteristic cross-sectional dimension) of a locking aperture, generally so that the threaded fastener fits closely into the locking aperture. Exemplary diameters that may be suitable are presented above in Section II. The threaded fastener may include only one continuous or interrupted external thread or may include two or more interspersed or spaced external threads. The external thread may have a pitch that corresponds to the pitch of an internal thread (s) of the locking aperture (see Section II for exemplary pitches). The external thread may have a depth that is about the same as the depth of a corresponding internal thread, substantially less, or substantially greater, such as about 50%, 100%, 200%, or 400% greater. The external thread may be complementary in profile to the internal thread or may have a distinct profile. The external thread may be relatively deep, such as a thread for cancellous bone (generally with a greater pitch), or may be relatively shallow, such as a thread for cortical bone or a machine thread (generally with a lesser pitch). Further aspects of threaded fasteners that may be suitable for locking apertures are described elsewhere in the present teachings, such as in Section VII, among others.

IV. Composition of System Components

Each system component (e.g., orthopedic rod, fasteners, etc.) may be formed of any suitable biocompatible material (s). Exemplary biocompatible materials include (1) metals (for example, titanium or titanium alloys; alloys with cobalt and chromium (cobalt-chrome); stainless steel; etc.); (2) plastics (for example, ultra-high molecular weight polyethylene (UHMWPE), polymethylmethacrylate (PMMA), polytetrafluoroethylene (PTFE), polyetheretherketone (PEEK), and/or PMMA/polyhydroxyethylmethacrylate (PHEMA)); (3) ceramics (for example, alumina, beryllia, calcium phosphate, and/or zirconia, among others); (4) composites; (5) bioresorbable (bioabsorbable) materials or polymers (for example, polymers of α-hydroxy carboxylic acids (e.g., polylactic acid (such as PLLA, PDLLA, and/or PDLA), polyglycolic acid, lactide/glycolide copolymers, etc.), polydioxanones, polycaprolactones, polytrimethylene carbonate, polyethylene oxide, poly-β-hydroxybutyrate, poly-β-hydroxypropionate, poly-δ-valerolactone, other bioresorbable polyesters, and/or natural polymers (such as collagen or other polypeptides, polysaccharides (e.g., starch, cellulose, and/or chitosan), any copolymers thereof, etc.); (6) bone tissue (e.g., bone powder and/or bone fragments); and/or the like. In some examples, these materials may form the body of a rod and/or fastener, and/or a coating thereon. The rod and fasteners of an implant system may be formed of the same material(s) or different materials. Exemplary configurations with different materials may include a rod and fasteners formed of different metals.

V. Installation of Orthopedic Rods

Orthopedic rods described herein may be installed in a bone (or bones) by any suitable method(s). Exemplary steps that may be included in a method of installation are described below. The steps may be performed in any suitable combination, in any suitable order, and any suitable number of times.

A bone may be selected for installation of an orthopedic rod. The bone may be any suitable bone, for example, a long bone having a medullary canal (and/or any bone engineered to have a cavity for receiving an orthopedic rod). Exemplary long bones that may be suitable include a bone of the arms (such as a humerus, a radius, an ulna, etc.), a bone of the legs (such as a femur, a tibia, a fibula, etc.), or the like. The bone may have any suitable condition to be treated with the rod, such as a fracture, a malunion, a nonunion, a cut (an osteotomy), a structural weakness, an undesirable length and/or angulation, and/or the like. The condition may affect any suitable portion of the bone, such as a diaphyseal (shaft) and/or a metaphyseal (end) region of the bone. In exemplary embodiments, the condition affects the proximal (and/or distal) region of a humerus or tibia.

The bone may be prepared for receiving the rod. The preparation may include any suitable surgical procedures for monitoring a patient's vital signs, preparing a sterile field, debriding and disinfecting an injury, etc. The preparation also or alternatively may include modifying the medullary canal of a bone, for example, forming a hole in the end of the bone to lengthen the medullary canal and render the canal externally accessible (opening the medullary canal to the exterior), broaching and/or reaming the medullary canal to widen and/or define the diameter, cross-sectional shape, and/or longitudinal shape of the canal, shortening the canal by cutting off the end and/or removing an internal segment of the bone, and/or the like. In some examples, the preparation may remove the head of the bone (and, optionally, a suitable length of the neck of the bone adjacent the head), to create a missing region of the bone. Alternatively, or in addition, removal may be performed at least partially by an injury to the bone. The medullary canal may be widened, shaped, and/or accessed in and/or from any suitable end of the bone, such as a proximal and/or distal region and/or end of the bone. In exemplary embodiments, the medullary canal of the humerus may be accessed from a proximal end (or a distal end) of the humerus, or the medullary canal of the tibia may be accessed from a proximal end of the tibia. In some embodiments, the tibia may be accessed from its distal end, such as to allow placement of a rod for a tibiocalcaneal fusion.

The site of installation may be measured to determine a size of rod that would be suitable. This measurement may include measuring a width and/or length of the medullary canal (with or without preparation to modify its size and/or shape), a width and/or length of a remaining portion and/or end surface of the bone, a spacing of the remaining end surface of the bone from one or more adjacent skeletal members (other bones or bone fragments), and/or the like. In some examples, measurement may be performed with a measuring device, such as a height gauge. Accordingly, the measuring device may be a trial rod and/or implant (such as a prosthesis) that generally replicates a potential disposition of a more permanent rod and/or implant. The measuring device may include a measurement mechanism that indicates one or more measured dimension(s) and/or a suitable size (or identity) of an implant prosthesis (or implant component), among others. Measurement also or alternatively may be performed, for example, with a measurement device (such as a ruler, a tape measure, a spacer element, calipers, etc.) or may be determined from a template visible by radiography, fluoroscopy, etc. Further aspects of measuring devices and trial implants are described in U.S. patent application Ser. No. 11/078,068, filed Mar. 11, 2005, which is incorporated herein by reference.

A rod may be selected (obtained). Selection may include selecting a rod having one or more locking apertures, such as any of the locking apertures described in the present teachings. Selection also may include selecting a rod configured for use on the left or the right side of the body, but not both. The rod may be selected according to the orthopedic condition to be treated, for example, based on the bone to be treated, the injury site(s) within the bone, the size of the medullary canal of the bone, etc. The components of rods having two or more components may be selected separately, for example, selecting a stem portion to match a desired length of the shaft of a bone and selecting a head portion to match a desired size and/or configuration of the end of a bone. The step of selecting a rod having two or more components also may include and/or be complemented by a step of assembling the rod by joining the two or more components, before, during, or after securing the rod to bone.

The rod may be placed in the medullary canal of the bone, generally after preparation of the canal (if performed). The rod may be placed into the canal from a proximal (antero-grade direction) or distal (retrograde direction) end of the bone. Placement may position the rod completely within the bone, in adjacent bones, or substantially in the bone but extending out of the bone. In some examples, the rod may be forced into the bone, for example, by hammering, or may slide readily into the bone. Moreover, placement may be facilitated by a wire along which the rod, if cannulated, may slide. Furthermore, placement may be monitored, guided, and/or confirmed using radiography and/or fluoroscopy, among others.

The rod may be secured to the bone using one or more fasteners. In some examples, the fasteners may be placed into and/or through apertures in the rod using a guide (or jig) connected to the rod. The fasteners may be placed into locking and/or nonlocking apertures of the rod in any suitable order. In some examples, a threaded fastener(s) may be disposed in threaded engagement with ("threaded into") a locking aperture(s) such that the threaded fastener is received in and engages less than all of the internal threads of the locking aperture, for example, only one of two or more alternative internal, interspersed threads. Alternatively, or in addition, a threaded fastener(s) may be threaded into threaded engagement with a locking aperture(s) by random selection of and entry into a subset (e.g., only one) of two or more thread leads disposed adjacent and/or around the perimeter of the entry side of the locking aperture(s).

A threaded fastener may be placed into a locking aperture in any suitable fashion. Generally, the threaded fastener is advanced first into a near side of the bone and then into the locking aperture. The threaded fastener may be advanced only into the aperture and not beyond the aperture or may be advanced farther beyond the aperture into a far side of the bone opposing the near side across the medullary canal. Advancement into the near side of the bone may be rotational and/or translational. Rotational advancement may be into a preformed pilot hole in bone or may be performed with a self-drilling threaded fastener. Translational advancement may be into a larger preformed hole in bone that is not engaged by an external thread of the fastener, allowing the fastener to slide linearly along the hole. With rotational advancement, the threaded fastener may arrive at the locking aperture with a rotational disposition that is not predefined, which may allow random selection of a thread lead(s) and/or internal thread(s). In any event, placement of the threaded fastener into the locking aperture may produce threaded engagement between the threaded fastener and the locking aperture, between the threaded fastener and near-side bone, and/or between the threaded fastener and far-side bone, among others.

The rod may be left in the bone for any suitable length of time. In some examples, the rod may be left in place relatively permanently. In some examples, the rod may be removed after the orthopedic condition improves sufficiently (e.g., a fractured bone heals).

Further aspects of rod installation that may be suitable for the methods of the present teachings are described in U.S. Pat. No. 5,472,444, issued Dec. 5, 1995, and U.S. Pat. No. 6,494,913, issued Dec. 17, 2002, each of which is incorporated herein by reference.

VI. Kits

The orthopedic rods may be provided in kits. A kit may include one or more rods of the same and/or different sizes/shapes. The kit also may include fasteners for locking and/or nonlocking apertures of the rod(s), a positioning jig(s), a drill/fastener guide(s), a measuring device(s), a drill(s), a reamer(s), a broach(es), instructions for use, and/or the like. Some or all of the kit components may be provided in a sterile condition, for example, packaged to maintain sterility.

In some examples, the kit may include one or more positioning jigs and/or guides. The jig and/or guide may be configured to be connected to a rod, such as through an end of the rod. The jig/guide also or alternatively may be configured to facilitate adjusting the height (axial disposition) and/or angular disposition of the rod relative to bone, through, for example, reference marks, axial/angular adjustment mechanisms, and/or alignment structures, among others, disposed on the jig/guide. In some examples, the jig/guide may include a guide structure (such as a cannula) configured to direct a hole-forming device, such as a drill, and/or to direct placement of fasteners into openings of the rods.

Further aspects of jigs/guides are described in U.S. Pat. No. 6,494,913, issued Dec. 17, 2002, which is incorporated herein by reference.

VII. Examples

The following examples describe selected aspects of the present teachings, including exemplary orthopedic rods and fasteners, and exemplary methods of using orthopedic rods. These examples are included for illustration and are not intended to limit or define the entire scope of the present teachings.

Example 1

Exemplary Intramedullary Rod

This example describes an exemplary intramedullary rod for bone fixation and an exemplary bone screw for connecting the rod to bone by threaded engagement with a multi-threaded aperture of the rod; see FIGS. 2-5. Other aspects of the intramedullary rod and bone screw shown in these figures are described elsewhere in the present teachings, particularly near the beginning of the Detailed Description in relation to FIG. 1.

FIG. 2 shows intramedullary rod 24 in the absence of bone and fasteners. The rod may have any suitable shape. For example, the rod may have a leading end 48 that is placed first into the medullary canal of a bone, in an anterograde (proximal to distal) (or retrograde (distal to proximal)) approach, and a trailing end 44 disposed opposite the leading end. The trailing end may be generally planar or flat, as shown here, or may be rounded. The rod may taper toward the leading end, along a portion or all of its length, such that the trailing end is larger in diameter than the leading end and to restrict entry of the rod into a tapered medullary canal. The rod may be divided conceptually into a leading portion 60 for placement into a shaft region of a bone and a trailing portion 62 (a butt portion) for placement into a head region of the bone. In other embodiments, the rod may be configured to be placed only into the shaft, only into the head, or into the shaft and both opposing heads of a bone, among others. In addition, the rod may be linear or bent (including discontinuously or angularly bent and continuously or curvilinearly bent, among others).

Rod 24 may include a longitudinal passage and a plurality of transverse apertures that facilitate positioning and/or securing the rod. For example, the rod may be hollow (a cannulated rod), with a longitudinal passage 64 that extends lengthwise through the rod such that the rod is hollow along its entire length. The passage may have a uniform diameter or may vary in diameter as the passage extends along the rod. For example, the passage may taper or may narrow in a stepwise fashion (as shown here) toward the tip of the rod. The passage may, for example, allow the rod to be placed over and slide along a pre-positioned guide wire (or may allow insertion of the guide wire through a pre-positioned rod). The rod also may include a plurality of transverse apertures, including trailing (proximal) apertures 42 and leading (distal) apertures 46. Each aperture may be threaded internally (locking) or nonthreaded internally (nonlocking). In exemplary embodiments, one or more (or all) trailing apertures may be threaded internally and one or more (or all) leading apertures may be nonthreaded internally (or vice versa). Here, each of the larger trailing apertures is multi-threaded and each of smaller distal apertures 46 is nonthreaded internally. In some examples, the rod may include one or more transverse openings of smaller diameter, such as a hole 66 for receiving a wire or other fastener (e.g. a bone screw) of relatively smaller diameter.

Apertures 42 and 46 may have any suitable angular disposition in the rod. For example, some or all of the apertures may define an axis that is parallel to the same plane (e.g., an orthogonal plane), as shown here, such that the apertures all extend orthogonally to the same axis (e.g., a long axis defined by the rod). However, in some embodiments, one or more of the apertures may be disposed obliquely relative to the long axis defined by the rod and/or not parallel to the same (e.g., orthogonal) plane, such that one or more of the apertures have a proximal-distal slant when the rod is installed in a long bone. In addition, one or more of the apertures may be rotated relative to one another about the long axis, for fastener placement into the apertures from different sides of a bone (e.g., see FIG. 1). Moreover, each aperture may be structured to receive a fastener from only one direction or from opposing directions defined by the aperture.

FIG. 3 shows a sectional view of rod 24 taken longitudinally through the rod in an end region of proximal portion 62. This fragmentary view includes only the pair of locking apertures 42 disposed closest to the trailing end of the rod. Each locking aperture 42 may have an internal thread structure 80 with a multi-threaded configuration centered around a central axis 81 defined by the aperture. For example, the multi-threaded configuration may include a plurality of internal threads 82, 84, 86 interspersed with one another along the aperture. In some embodiments, the internal threads may be axially offset, parallel to the central axis of the aperture, by a distance approximately equal to the pitch of the internal threads divided by the number of internal threads, for example, here, the three internal threads are offset by the thread pitch divided by three. Accordingly, adjacent segments (related by one complete turn and indicated for illustration at 88, 89) of one of the internal threads, may be separated by a segment of each of the other internal threads (e.g., segments 90 and 92 between segments 88, 89 in the present illustration). Each of the internal threads may have the same pitch and may extend along side-by-side, non-intersecting helical paths in the aperture, as shown in the present illustration, or the helical paths may intersect one another. In any event, the internal threads may provide alternative options for threaded engagement with a single external thread of a fastener and/or may provide multi-threaded engagement between a multi-threaded aperture (two or more internal threads) and a multi-threaded fastener (two or more external threads).

Each internal thread may be interrupted by intersection with longitudinal passage 64 of the rod. Accordingly, the internal thread may have a discontinuous structure created by two or more discrete, spaced thread segments positioned along portions of the same helical path. For example, here, internal thread 86 includes a pair of longer thread segments 94, 96 that oppose one another across passage 64, and a shorter thread segment 98. However, for the purposes of the present teachings, segments 94-98 are considered to be part of the same internal thread because they lie on the same helical path.

The longitudinal passage (64) may have any suitable diameter relative to the diameter of the aperture that the passage intersects. For example, in rod 24 the passage is smaller in diameter than the aperture to create one or more discrete thread segments (such as segment 98) disposed centrally in the aperture and extending only partway around the aperture. Discrete thread segments disposed more toward the exterior of the rod may be longer (e.g., segments 94 and 96), having thread flutes that extend partially or completely around the aperture, one or more times. In some examples, the passage of the rod may be wider than the aperture, such that a central section of the aperture does not include a portion of an internal thread, or the internal thread may be missing from the central section of the aperture for any other reason.

FIG. 3 also shows other structural features of rod 24. The rod may have a monolithic structure (a one-piece or unitary construction). Alternatively, the rod may be constructed of two or more components connected to one another in a movable or fixed relationship. For example, here, rod 24 includes a body component 100 and a cap component 102 fixed to an end of the body component. The body or and/or cap component may define an internal thread 104, which may be centered around a regional central axis 106 of the rod, for threaded engagement with a plug (e.g., to close the trailing end of the rod), a guide device (e.g., for drill and/or fastener placement), and/or a positioning jig (and/or a graspable handle) (e.g., to facilitate positioning the rod during installation).

Figure 4:
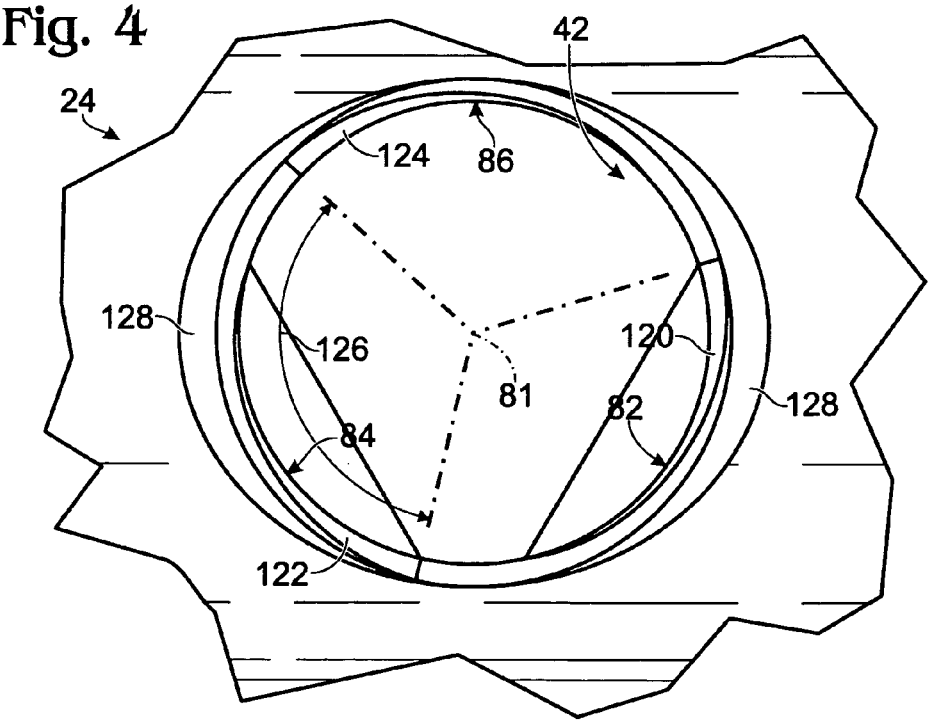
FIG. 4 is a fragmentary external view of the intramedullary rod of FIG. 2, taken generally along line 4-4 of FIG. 3 toward one of the proximal apertures having a multi-threaded structure.

FIG. 4 shows an external view of rod 24 taken parallel to central axis 81 of trailing aperture 42 having a multi-threaded structure. Each internal thread 82-86 may extend to a corresponding thread lead 120, 122, 124 disposed adjacent the same opposing end (an entry side and/or an exit side) of the aperture. The thread leads may be disposed at distinct positions around the aperture (and generally at about the same axial position), or at the same (circumferential) position around the aperture (and generally with different axial positions, i.e., with different axial offsets parallel to the central axis of the aperture. Each thread lead may be a leading end disposed adjacent an entrance to the aperture and may provide an entry site at which an external thread (e.g., a helical rib or ridge) of a fastener may be received for advancement along a helical path defined by a helical flute(s) of one of the internal threads. The thread of a threaded fastener thus may have more options for being received in improved registration with one of the thread leads (and corresponding internal thread), relative to an aperture with only one internal thread having the same pitch. In other words, a threaded fastener may start threading into the aperture at any of several places around the perimeter of the aperture (and/or along the aperture), meaning that it may be unnecessary to turn the screw as far before it begins to engage an internal thread. The thread leads may be spaced equally around the aperture, for example, here, about 120 degrees apart, indicated at 126, with three internal threads.

The aperture may include a counterbore(s) 128 disposed adjacent one or at both ends of the aperture. The counterbore may function, for example, to facilitate guiding a fastener into the aperture, such that the fastener is centered in relation to the aperture. The aperture may be configured to receive a fastener from only one end (one entrance) of the aperture or from either opposing end (two entrances).

In an exemplary embodiment, intended for illustration only, the aperture may have the following dimensions: a helical flute with a width of about 0.010 inch, a major diameter of about 0.215 inch, a minor diameter of about 0.205 inch, and a pitch of each internal thread (helical flute) of about 0.087 inch.

Figure 5:
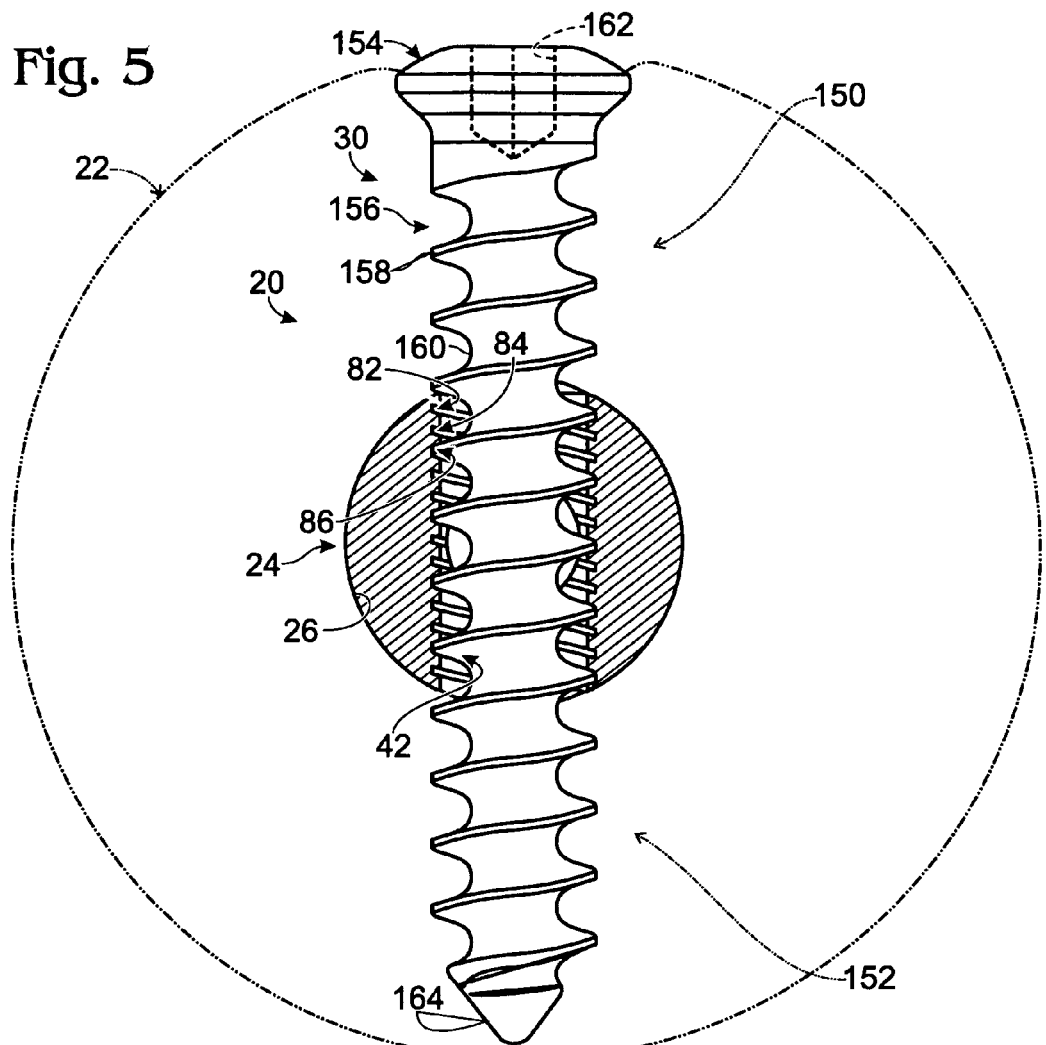
FIG. 5 is a somewhat schematic, cross-sectional view of the orthopedic implant system of FIG. 1, taken generally along line 5-5 of FIG. 1 through a bone screw disposed in threaded engagement with the most proximal multi-threaded aperture of the intramedullary rod.

FIG. 5 shows a somewhat schematic, cross-sectional view of implant system 20, taken generally along line 5-5 of FIG. 1 with the system disposed in bone. In this view, bone screw 30 is disposed in humerus 22, extending through intramedullary rod 24 and medullary canal 26, in threaded engagement with aperture 42 of the rod and with opposing portions 150, 152 of the humerus.

Screw 30 may be constructed for selective engagement with a subset of internal threads 82-86 of aperture 42. The screw may have a head 154 and a shank 156 extending from the head. The shank may include an external thread(s) 158 formed as a helical rib(s) extending continuously or discontinuously along the shank. The external thread(s) may have a pitch and a major diameter that correspond to the pitch and major diameter of each internal thread 82-86. Accordingly, external thread 158 may be received in only one of the internal threads when the bone screw is advanced into threaded engagement with the aperture. For example, here, external thread 158 is received in internal thread 86 such that internal threads 82 and 84 to not engage the external thread, but instead are opposed to a helical flute 160 defined by shank 156.

External thread 158 may have any suitable depth relative to the depth of internal threads 82-86. For example, here, the external thread may be relatively deep to provide sufficient engagement with bone, particularly cancellous bone. In addition, the internal threads may be relatively shallow, such as less than about one-half the depth of the external thread. The use of shallow threads may permit two or more internal threads to be formed in an interspersed relationship along the aperture. (A deeper internal thread may limit the formation of two or more interspersed internal threads.) Furthermore, shallow internal threads may impose fewer limitations on how a locking aperture is used. For example, shallow internal threads may permit nonlocking placement of a cancellous bone screw through a locking aperture when the cancellous bone screw has a diameter that is only slightly smaller than the diameter of a corresponding bone screw that locks to the aperture.

Bone screw 30 may have any other suitable structure. For example, head 154 may include a socket 162 for receiving a driver and/or may have external driver engagement structure, such as a polygonal (e.g., hexagonal) head. Bone screw 30 also may include a tip 164 opposing the head. The tip may be blunt or sharp. Furthermore, the tip may define an angle with the long axis of the screw of greater than about 30 degrees. In some examples, the tip may include a nonthreaded region. The nonthreaded region may, for example, be frustoconical (or conical). The bone screw may be solid or may be hollow, for example, with a cannulation extending longitudinally between opposing ends of the bone screw.

Example 2

Exemplary Relationships between Internal and External Threads

Figure 6:
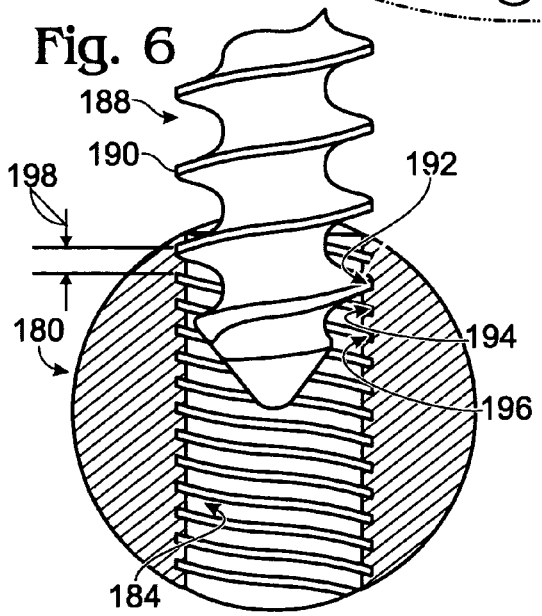
FIG. 6 is a somewhat schematic, cross-sectional view of an exemplary rod member, taken through a multi-threaded aperture of the rod member, with an exemplary bone screw advanced incompletely into the multi-threaded aperture, in accordance with aspects of the present teachings.
Figure 7:
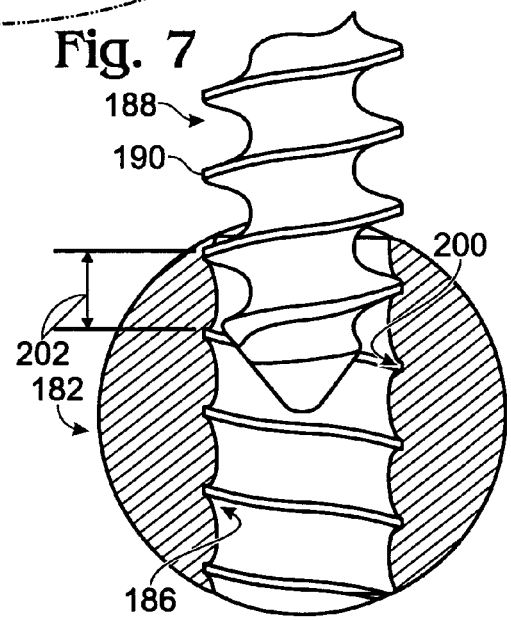
FIG. 7 is a somewhat schematic, cross-sectional view of another exemplary rod member, taken through a single-threaded aperture of the rod member, with the bone screw of FIG. 6 advanced incompletely into the single-threaded aperture, in accordance with aspects of present teachings.

This example describes exemplary relationships between the internal thread structure of a rod aperture and an external thread of a threaded fastener, and how these relationships may affect the threadability of the threaded fastener into the rod aperture; see FIGS. 6 and 7.

FIGS. 6 and 7 show somewhat schematic representations of orthopedic rods 180, 182 including respective multi-threaded aperture 184 and single-threaded aperture 186, each having the same thread pitch. Each aperture is shown with an exemplary bone screw 188 at an early stage of threaded management into the aperture via an external thread 190.

In aperture 184, the external thread can be received alternatively in each of three internal threads 192-196 separated by only one-third, indicated at 198, of the pitch of each internal thread. Accordingly, as bone screw 188 reaches aperture 184 during placement of the bone screw into the aperture from bone, external thread 190 should be out of registration axially with the aperture by no more than about one-half of the distance between adjacent internal threads, namely, about one-sixth of the thread pitch. A relatively small adjustment in the relative positions of the bone screw and aperture during screw advancement thus should correct any misregistration.

In aperture 186, the external thread can be received by only one internal thread 200 having a pitch indicated at 202. Accordingly, as bone screw 188 reaches aperture 186 during placement of the bone screw into the aperture from bone, external thread 190 should be out of registration by no more than about one-half of the distance between adjacent internal threads, namely, about one-half of the thread pitch. A relatively larger adjustment (about three times the distance for aperture 184) thus should correct any misregistration. This relatively larger adjustment may involve damage to bone (and/or the rod) as the bone screw and aperture are forced into registration. As a result, use of aperture 184 may be desirable over aperture 186.

Example 3

Bone Screw for Locking Apertures

The following example describes an exemplary bone screw that may be suitable for insertion into, and/or threaded engagement with, the locking (and/or nonlocking) apertures of the present teachings.

The bone screw may have a shank with an external thread (a helical rib) extending along a portion or at least substantially all of the shank. The external thread may have a pitch that is about the same as the pitch of the internal thread(s) of an aperture into which the bone screw is placed. The external thread may include a land of measurable width (measured parallel to the long axis of the screw). Furthermore, the external thread may extend adjacent an axially offset helical flute. The flute may include an arcuate profile and/or an angular profile. Opposing walls of the flute (the walls of adjacent ridges) may define any suitable angle.

The bone screw may have a shank with a major diameter and a minor diameter. The major diameter may be defined as the crest-to-crest distance between opposing thread segments of the external thread measured orthogonally through the central axis of the bone screw. The minor diameter may be measured in generally the same way as the trough-to-trough distance between opposing grooves of the external thread. The major diameter may be substantially larger than the minor diameter, for example, at least about 25%, 35%, or 50% larger, to create a cancellous bone screw with a relatively deep thread.

In an exemplary embodiment, intended only for illustration, the bone screw may have the following dimensions: a pitch of about 0.087 inch, a major diameter of about 0.211 inch, a minor diameter of about 0.109 inch, a tip angle relative to the long axis of about 36 degrees, a land width of about 0.008 inch, a flute radius of about 0.032 inch, and a flute wall-to-wall angle of about 35 degrees.

Further aspects of threaded fasteners that may be suitable for use with the orthopedic rods of the present teachings are described in U.S. Provisional Patent Application Ser. No. 60/729,373, filed Oct. 21, 2005, which is incorporated herein by reference.

Example 4

Orthopedic Rod with a Tapered Internal Thread

This example describes an exemplary orthopedic rod having an aperture an internal thread that tapers.

The orthopedic rod may include a locking aperture having an internal thread that varies in width (as measured parallel to the central axis of the aperture). In particular, the internal thread may be wider towards the entry side of the aperture, such that the internal thread tapers as the aperture extends away from the entry side. Accordingly, a bone screw or other threaded fastener may thread more readily into the internal thread where the helical groove of the internal thread is wider, to provide a looser fit. The bone screw then may be advanced into a tighter fit with the internal thread where the helical groove of the internal thread is narrower, away from the entry side of the aperture. The thread (of the rod or screw) and/or bone thus may be deformed gradually by screw advancement. Axial registration of mated threads thus may be achieved progressively during advancement of the bone screw.

Further aspects of orthopedic rods having apertures with a tapered thread structure are described in U.S. Provisional Patent Application Ser. No. 60/729,373, filed Oct. 21, 2005, which is incorporated herein by reference.

The disclosure set forth above may encompass multiple distinct inventions with independent utility. Although each of these inventions has been disclosed in its preferred form(s), the specific embodiments thereof as disclosed and illustrated herein are not to be considered in a limiting sense, because numerous variations are possible. The subject matter of the inventions includes all novel and nonobvious combinations and subcombinations of the various elements, features, functions, and/or properties disclosed herein. The following claims particularly point out certain combinations and subcombinations regarded as novel and nonobvious. Inventions embodied in other combinations and subcombinations of features, functions, elements, and/or properties may be claimed in applications claiming priority from this or a related application. Such claims, whether directed to a different invention or to the same invention, and whether broader, narrower, equal, or different in scope to the original claims, also are regarded as included within the subject matter of the inventions of the present disclosure.

We claim:

1. A method of installation of a rod member in a bone, comprising:

placing a rod member along a medullary canal of a bone, the rod member defining one or more transverse apertures, at least one of the transverse apertures being a locking aperture having opposing ends and including at least two internal threads following distinct helical paths centered about a same axis, each internal thread having a distinct thread lead disposed adjacent a same opposing end of the locking aperture; and attaching the rod member to the bone with a fastener (a) capable of alternative threaded engagement with each of the internal threads of the locking aperture and (b) disposed in threaded engagement with only one of the internal threads, to lock the fastener to the rod member, wherein the fastener includes a head and a shank, wherein the shank has a single external thread formed on leading, central, and trailing portions of the shank, wherein the single external thread has a substantially uniform pitch and is substantially deeper than each of the internal threads, and wherein the step of attaching results in the single external thread being in threaded engagement with a thread of about a same depth formed in bone adjacent the opposing ends of the locking aperture and in threaded engagement with an internal thread of the locking aperture.

2. The method of claim 1, wherein the step of placing a rod member includes a step of spanning a discontinuity in the bone with the rod member.

3. The method of claim 1, wherein the rod member is a stem of a prosthetic implant, further comprising a step of replacing a head of the bone with a prosthetic head of the prosthetic implant.

4. The method of claim 1, wherein the step of placing a rod member includes a step of placing a rod member in which the locking aperture defines a central axis, wherein the at least two internal threads are a number of threads each having a pitch, and wherein the at least two internal threads are offset from one another in a direction parallel to the central axis by a distance substantially equal to the pitch divided by the number.

5. The method of claim 1, wherein the step of placing a rod member includes a step of placing a rod member in which the at least two internal threads do not intersect one another.

6. The method of claim 1, wherein the step of placing a rod member includes a step of placing a rod member in which the locking aperture includes at least three internal threads each following a distinct helical path and each extending to a distinct thread lead disposed adjacent the same opposing end of the locking aperture, and wherein the step of attaching the rod member disposes an external thread of the fastener in threaded engagement with only one of the at least three internal threads.

7. The method of claim 1, wherein the step of placing a rod member includes a step of placing a rod member defining a passage extending lengthwise through the rod member.

8. The method of claim 1, wherein the step of placing a rod member includes a step of placing a rod member defining a longitudinal axis, and wherein the locking aperture extends in a direction that is orthogonal to the longitudinal axis.

9. The method of claim 1, wherein the rod member has a trailing portion of greater diameter and including two or more locking apertures, and wherein the step of attaching the rod member is performed with the two or more locking apertures disposed near or in a head of the bone.

10. The method of claim 1, wherein the average depth of the external thread is at least about twice the average depth of each internal thread.

11. The method of claim 1, wherein the step of attaching the rod member is performed with a fastener including an external thread that is interrupted such that the external thread includes a plurality of discrete thread segments each extending along discrete portions of a same helical path.

12. A method of installation of a rod member in a bone, comprising:

placing a rod member along a medullary canal of a bone, the rod member defining one or more transverse apertures configured to receive fasteners that connect the rod member to the bone, at least one of the transverse apertures being a locking aperture including at least two internal threads that are interspersed with one another and that are centered about a same axis; and attaching the rod member to the bone with a fastener (a) capable of alternative threaded engagement with each of the internal threads and (b) disposed in threaded engagement with only one of the internal threads, to lock the fastener to the rod member, wherein the fastener includes a head and a shank, wherein the shank has a single external thread formed on leading, central, and trailing portions of the shank, wherein the single external thread has a substantially uniform pitch and is substantially deeper than each of the internal threads, and wherein the step of attaching results in the single external thread being in threaded engagement with a thread of about a same depth formed in bone adjacent opposing ends of the locking aperture and in threaded engagement with an internal thread of the locking aperture.

13. The method of claim 12, wherein the step of attaching the rod member is performed with a fastener including an external thread that is interrupted such that the external thread includes a plurality of discrete thread segments each extending along discrete portions of a same helical path.

14. The method of claim 12, wherein the average depth of the external thread is at least about twice the average depth of each internal thread.

* * * * *